United States Patent [19]

Pasternak et al.

[11] Patent Number: 5,004,861

[45] Date of Patent: * Apr. 2, 1991

[54] PROCESS FOR PERVAPORIZATION USING MEMBRANE SEPARATING MEANS

[75] Inventors: Mordechai Pasternak, Spring Valley; Craig R. Bartels; John Reale, Jr., both of Wappingers Falls, all of N.Y.

[73] Assignee: Texaco Inc., White Plains, N.Y.

[*] Notice: The portion of the term of this patent subsequent to Jan. 17, 2006 has been disclaimed.

[21] Appl. No.: 214,987

[22] Filed: Jul. 5, 1988

[51] Int. Cl.$^5$ .................. C07C 7/144; B01D 13/00
[52] U.S. Cl. ............................ 585/818; 585/865; 210/644; 210/654
[58] Field of Search ................. 208/308, 33, 321; 585/818, 865; 210/634, 644, 640, 654; 55/158

[56] References Cited

U.S. PATENT DOCUMENTS 4,910,344 3/1990 Pasternak et al. .

*Primary Examiner*—Anthony McFarlane
*Attorney, Agent, or Firm*—Robert A. Kulason; James J. O'Loughlin; Carl G. Seutter

[57] ABSTRACT

Water is separated from an MEK toluene dewaxing solvent by pervaporation through a polyvinyl alcohol membrane (optionally containing polyacrylic acid) mounted on a polyacrylonitrile support layer.

9 Claims, No Drawings

PROCESS FOR PERVAPORIZATION USING MEMBRANE SEPARATING MEANS

FIELD OF THE INVENTION

This invention relates to solvent dewaxing. More particularly it relates to a process for removing water from mixture of hydrocarbons and organic oxygenates—such as the toluene-methyl ethyl ketone solvent used in MEK dewaxing of hydrocarbon lubricating oils.

BACKGROUND OF INVENTION

As is well known to those skilled in the art, it is possible to remove water from mixtures thereof with organic liquids by various techniques including adsorption or distillation. These conventional processes, particularly distillation, are however characterized by high capital cost. In the case of distillation for example the process requires expensive distillation towers, heaters, heat exchangers (reboilers, condensers, etc.), together with a substantial amount of auxiliary equipment typified by pumps, collection vessels, vacuum generating equipment, etc.

Such operations are characterized by high operating costs principally costs of heating and cooling plus pumping, etc.

Furthermore the properties of the materials being separated, as is evidenced by the distillation curves, may be such that a large number of plates may be required, etc. When the material forms an azeotrope with water, additional problems may be present which for example, could require that separation be effected in a series of steps (e.g. as in two towers) or by addition of extraneous materials to the system.

There are also comparable problems which are unique to adsorption systems.

It has been found to be possible to utilize membrane systems to separate mixtures of miscible liquids by pervaporation. In this process, the charge liquid is brought into contact with a membrane film; and one component of the charge liquid preferentially permeates the membrane. The permeate is then removed as a vapor from the downstream side of the film—typically by sweeping with a carrier gas or by reducing the pressure below the vapor pressure of the permeating species.

Illustrative membranes which have been employed in prior art techniques include those set forth in the following table:

TABLE

| Separating Layer | References |
| --- | --- |
| Cross-linked polyvinyl alcohol | Eur. Patent 0 096 339 to GFT as assignee of Bruschke |
| Cellulose triacetate | Wentzlaff, Boddeker & Hattanback J. Memb Sci 22, 333 (1985) |
| Polyacrylonitrile | Neel, Aptel, & Clement Desalination 53, 297 (1985) |
| poly (maleimide-acrylonitrile) | Yoshikawa et al J. Pol. Sci. 22,2159 (1984) |

The cost effectiveness of a membrane is determined by the selectivity and productivity. Of the membranes commercially available, an illustrative membrane of high performance is that disclosed in European patent 0 096 339 A2 of GFT as assignee of Bruschke—published Dec. 31, 1983.

European Patent 0 096 339 A2 to GFT as assignee of Bruschke discloses, as cross-linking agents, diacids (typified by maleic acid or fumaric acid); dihalogen compounds (typified by dichloroacetone or 1,3-dichloroisopropanol); aldehydes, including dialdehydes, typified by formaldehyde. These membranes are said to be particularly effective for dehydration of aqueous solutions of ethanol or isopropanol.

This reference discloses separation of water from alcohols, ethers, ketones, aldehydes, or acids by use of composite membranes. Specifically the composite includes (i) a backing, typically about 120 microns in thickness, on which is positioned (ii) a microporous support layer of a polysulfone or a polyacrylonitrile of about 50 microns thickness, on which is positioned (iii) a separating layer of cross-linked polyvinyl alcohol about 2 microns in thickness.

Polyvinyl alcohol may be cross-linked by use of difunctional agents which react with the hydroxyl group of the polyvinyl alcohol. Typical cross-linking agent may include dialdehydes (which yield acetal linkages), diacids or diacid halides (which yield ester linkages), dihalogen compounds or epichlorhydrin (which yield either linkages) olefinic aldehydes (which yield ether/acetal linkages), boric acid (which yield boric ester linkages), sulfonamidoaldehydes, etc.

See also J. G. Prichard *Polyvinyl Alcohol, Basic Properties and Uses* Gordon and Breach Science Publishers, New York (1970) or C. A. Finch *Polyvinyl Alcohol, Properties and Applications* John Wiley and Sons, New York (1973).

It is an object of this invention to provided a novel process for separation of water from mixtures of hydrocarbon and organic oxygenate—typified by a mixture of toluene and methyl ethyl ketone. Other objects will be apparent to those skilled in the art.

STATEMENT OF THE INVENTION

In accordance with certain of its aspects, this invention is directed to a method of separating water from a charge aqueous mixture of hydrocarbon and organic oxygenate which comprises;

maintaining a non-porous membrane separating layer of (i) a blend of polyvinyl alcohol and a polyacrylic acid or (ii) cast polyvinyl alcohol which has been cross-linked with an aliphatic polyaldehyde containing at least three carbon atoms including those in said aldehyde groups;

maintaining a pressure drop across said non-porous separating layer;

passing a charge water-containing solution of hydrocarbon and organic oxgenate into contact with the high pressure side of said non-porous separating layer whereby at least a portion of said water in said charge aqueous mixture and a lesser portion of hydrocarbon and organic oxygenate in said charge aqueous mixture pass by pervaporation through said non-porous separating layer as a lean mixture containing more water and less hydrocarbon and organic oxygenate than are present in said charge aqueous mixture and said charge solution is converted to a rich liquid containing less water and more hydrocarbon and organic oxygenate than are present in said charge aqueous mixture;

recovering from the low pressure side of said non-porous separating layer said lean mixture containing more water and less hydrocarbon and organic oxygenate than are present in said charge aqueous mixture, said lean mixture being recovered in vapor phase at a pressure below the vapor pressure thereof; and recovering from the high pressure side of said non-porous separating layer said rich liquid containing a lower water content and a higher hydrocarbon and organic oxygenate content than are present in said charge aqueous mixture.

In accordance with certain of its other aspects, this invention is directed to use of a composite membrane comprising a porous inert support layer, preferably of polyacrylonitrile of molecular weight cutoff of 20,000-40,000 and a non-porous separating membrane layer of thickness of 1-10 microns of (i) a blend of polyvinyl alcohol and a polyacrylic acid or (ii) cast polyvinyl alcohol of molecular weight $\overline{M}_n$ of 20,000-200,000 which has been cross-linked, in the presence of acid catalyst, with an aliphatic polyaldehyde containing at least three carbon atoms including those in said aldehyde groups and thereafter cured at 100° C.-225° C.

DESCRIPTION OF THE INVENTION

The composite structure of this invention preferably includes a multi-layer assembly which in the preferred embodiment preferably includes a porous carrier layer which provides mechanical strength and support to the assembly. Clearly each of the components of the composite will be inert to the liquids with which they come into contact.

THE CARRIER LAYER

This porous carrier layer, when used, is characterized by its high degree of porosity and mechanical strength. It may be fibrous or non-fibrous, woven or non-woven. In the preferred embodiment, the carrier layer may be a porous, flexible, non-woven fibrous polyester.

A typically non-woven, thermally-bonded polyester carrier layer may be formulated of non-woven, thermally bonded strands and characterized by a fabric weight of 80±8 grams per square yard, a thickness of 4.2±0.5 mils, a tensile strength (in the machine direction) of 31 psi and (in cross direction) of 10 psi, and a Frazier air permeability of 6 cuft/min/sq. ft. @0.5 inches of water.

THE POROUS SUPPORT LAYER

The porous support layer of this invention maybe formed of a sheet of polymer membrane which is essentially inert with respect to (e.g. insoluble in) the hydrocarbon and the organic oxygenate which is used in practice of the process of this invention. The porous support layer may preferably be a membrane of polyacrylonitrile polymer. Typically the polyacrylonitrile may be of thickness of 40-80 microns, say 50 microns. The polyacrylonitrile is preferably characterized by a molecular weight cut-off of about 20,000-40,000.

The acrylonitrile polymers which may be employed may include those having repeating units of the formula:

THE SEPARATING LAYER

The separating layer which permits attainment of the separation in accordance with this invention includes a non-porous film of (i) a blend of polyvinyl alcohol and polyacrylic acid or (ii) cross-linked polyvinyl alcohol of thickness of about 1-10 microns preferably 1-5 microns, say 1.5 microns. The layer is formed from polyvinyl alcohol which has been prepared by hydrolysis of polyvinyl acetate-typically 50-100 w % hydrolyzed, preferably 90-100%, say 100% hydrolyzed. The charge polyvinyl alcohol has a molecular weight of 20,000-200,000 say 115,000. Typically it may be employed as a 5-10 w %, say 7 W % aqueous solution. A commercially available product which may be employed is the Aldrich brand of 100% hydrolyzed polyvinyl alcohol of molecular weight of about 115,000 as a 7 w % aqueous solution.

In accordance with certain of its aspects, when the separating layer is a blend or a mixture of vinyl alcohol polymer and a polymer of an acrylic acid such as acrylic acid or methacrylic acid, the charge from which the separating membrane is to be prepared may be an aqueous solution containing a vinyl alcohol polymer and a polymer of an acrylic acid. Typically the aqueous solution may contain 5-10 w %, say 7 w % of polyvinyl alcohol of molecular weight $\overline{M}_n$ of 20,000,-200,000, say 115,000 and 5-10 w %, say 7 w % of polyacrylic acid of molecular weight $\overline{M}_n$ of 90,000-300,000, say 250,000. The weight ratio of vinyl alcohol polymer to acrylic acid polymer may be 0.1-10:1, say 1:1.

It is a feature of this invention that when the separating layer is a membrane or sheet of cross-linked polyvinyl alcohol, it is formed in situ on the porous support layer. This is effected by use, as a cross-linking agent, of an aliphatic dialdehyde containing at least three carbon atoms. Preferably the aliphatic dialdehyde may contain 3-8 carbon atoms, most preferably 5 carbon atoms. Typical aliphatic dialdehydes which may be employed may include:

TABLE glutaraldehyde
2-hydroxyhexanedial-1,6
malonic dialdehyde
succinic dialdehyde
hexanedial-1,6

The preferred aliphatic dialdehyde is glutaraldehyde. Aldehydes falling outside the scope of this invention typified by formaldehyde, glyoxal, or succinic semi-aldehyde yield membranes which are characterized by unsatisfactory performance. Performance is judged by the ability of a membrane system to give a permeate containing more than 98 w % water (from a charge containing 1-2 w % water) with a flux of about 0.2 kilograms/meter²/hour (kmh) at a feed temperature of 60°-80° C. and with a permeate pressure of 2 mm.Hg and a condenser cooled by liquid nitrogen). Compositions falling outside the scope of this invention may be characterized by unsatisfactory selectivity or unsatisfactory productivity or both.

In situ cross-linking may be carried out by casting 5-10 w %, say 7 w % aqueous solution of polyvinyl alcohol which contains the aliphatic dialdehyde cross-linking agent. The mole ratio of cross-linking agent to polyvinyl alcohol may be 0.05-0.30, say 0.2.

Cross-linking is carried out, in the presence of acid catalyst, preferably inorganic acid. Sulfuric acid is preferred. Hydrochloric acid is much less preferred—because it yields membranes of poor selectivity, although the flux may be high.

It may be possible in one embodiment to cross-link the polyvinyl alcohol separating layer in one step by adding to the aqueous solution of polyvinyl alcohol and dialdehyde, the acid catalyst, preferably sulfuric acid, in mole ratio of acid to dialdehyde of 0.08–0.14, say 0.1.

When the separating layer is to be prepared from a mixture of vinyl alcohol polymer and acrylic acid polymer (as in a preferred embodiment) it is desirable to mix the aqueous solutions of polymers to form a mix containing both polymers.

The composite membrane, whether prepared from polyvinyl alcohol alone or from the blend of polyvinyl alcohol and polyacrylic acid, process may then be cured in an oven at 100° C.–225° C., say 125° C. for 1–30 minutes, say 2 minutes to yield a polyvinyl alcohol (optionally containing a polyacrylic acid) film having a thickness of 1–10 microns, say 2 microns.

It is possible that during curing, the polyvinyl alcohol and the polyacrylic acid may crosslink or otherwise react to form ester linkages.

THE COMPOSITE MEMBRANE

It is a feature of this invention that the composite membrane of this invention may comprise (i) an optional carrier layer, characterized by porosity and mechanical strength, for supporting support layer and a separating layer, (ii) a polyacrylonitrile porous support layer of molecular weight cut off of 20,000–40,000 and (iii) as a non-porous separating layer of (1) a blend of polyvinyl alcohol and polyacrylic acid or (2) polyvinyl alcohol of molecular weight $\overline{M}_n$ of 20,000–200,000 which has been cross-linked with an aliphatic dialdehyde containing 3–8 carbon atoms.

The composite membranes of this invention may be utilized in various configurations. It is, for example, possible to utilize the composite in a plate-and-frame configuration in which separating layers may be mounted on the porous support layer with the carrier layer.

It is possible to utilize a spiral wound module which includes a non-porous separating layer membrane mounted on a porous support layer and a carrier layer, the assembly being typically folded and bonded or sealed along all the edges but an open edge—to form a bag-like unit which preferably has the separating layer on the outside. A cloth spacer, serving as the permeate or discharge channel is placed within the bag-like unit. The discharge channel projects from the open end of the unit.

There then placed on one face of the bag-like unit, adjacent to the separating layer, and coterminous therewith, a feed channel sheet—typically formed of a plastic net.

The so-formed assembly is wrapped around a preferably cylindrical conduit which bears a plurality of perforations in the wall—preferably in a linear array which is as long as the width of the bag-like unit. The projecting portion of the discharge channel of the bag-like unit is placed over the preformations of the conduit; and the bag-like unit is wrapped around the conduit to form a spiral wound configuration. It will be apparent that, although only one feed channel is present, the single feed channel in the wound assembly will be adjacent to two faces of the membrane layer. The spiral wound configuration may be formed by wrapping the assembly around the conduit a plurality of times to form a readily handleable unit. The unit is fitted within a shell (in manner comparable to a shell-and-tube heat exchanger) provided with an inlet at one end and an outlet at the other. A baffle-like seal between the inner surface of the shell and the outer surface of the spiral-wound input prevents fluid from bypassing the operative membrane system and insures that fluid enters the system principally at one end. The permeate passes from the feed channel, into contact with the separating layer and thence therethrough, into the permeate channel and thence therealong to and through the perforations in the conduit through which it is withdrawn as net permeate.

In use of the spiral wound membrane, charge liquid is permitted to pass through the plastic net which serves as a feed channel and thence into contact with the non-porous separating membranes. The liquid which does not pass through the membranes is withdrawn as retentate. The liquid or vapor which permeates the membrane passes into the volume occupied by the permeate spacer and through this permeate channel to the perforations in the cylindrical conduit through which it is withdrawn from the system.

In another embodiment, it is possible to utilize the system of this invention as a tubular or hollow fiber. In this embodiment, the polyacrylonitrile porous support layer may be extruded as a fine tube with a wall thickness of typically 0.001–0.1 mm. The extruded tubes are passed through a bath of polyvinyl alcohol and glutaraldehyde which cross-links the polyvinyl alcohol. A bundle of these tubes after curing is secured (with an epoxy adhesive) at each end in a header; and the fibers are cut so that they are flush with the ends of the header. This tube bundle is mounted within a shell in a typical shell-and-tube assembly.

In operation, the charge liquid is admitted to the tube side and passes through the inside of the tubes. Permeate passes through the non-porous separating layer and permeate is collected in the shell side.

It is a feature of this invention that the novel membrane may be particularly useful in a pervaporation process for removing water form mixtures of hydrocarbons and organic oxygenates—such as the toluene-methyl ethyl ketone solvent used in MEK dewaxing of hydrocarbon oils.

These mixtures may commonly contain small quantities of immiscible water—typically up to 3–5 w % which may be derived from various sources. In the case of MEK dewaxing, it may be introduced as by contact with stripping steam etc.

Illustrative charge systems (which contain water) may include the following:

TABLE

|      |                          |
|------|--------------------------|
| (i)  | methyl ethyl ketone MEK  |
|      | toluene                  |
| (ii) | methyl ethyl ketone MEK  |
|      | toluene                  |
|      | benzene                  |
| (iii)| methyl ethyl ketone MEK  |
|      | benzene                  |
| (iv) | acetone                  |
|      | toluene                  |
| (v)  | acetone                  |
|      | gasoline                 |
| (vi) | acetone                  |
|      | heptane                  |
| (vii)| ethanol                  |
|      | gasoline                 |
| (viii)| methanol                |
|      | gasoline                 |
| (ix) | methanol                 |
|      | ethanol                  |
|      | gasoline                 |
| (x)  | ethyl acetate            |

TABLE-continued

| xylene |
| --- |

PERVAPORATION

It is a feature of the non-porous polyvinyl alcohol separating layer (preferably containing polyacrylic acid) that it is found to be particularly effective when used in a pervaporation process. In pervaporation, a charge liquid containing a more permeable and a less permeable component is maintained in contact with a non-porous separating layer; and a pressure drop is maintained across that layer. The charge liquid dissolves into the membrane and diffuses therethrough. The permeate which passes through the membrane and exits as a vapor may be recovered by condensing at low temperature or alternatively may be swept away by use of a moving stream of gas. Preferably, the permeate side of the membrane is maintained at a low pressure, typically 2 mm. Hg.

For general background on pervaporation, note U.S. Pat. Nos. 4,277,344; 4,039,440; 3,926,798; 3,950,247; 4,035,291; etc.

In practice of the pervaporation process of this invention, the charge solution at 40° C.-120° C., say 80° C. may be passed into contact with the non-porous separating layer of the membrane of this invention. A pressure drop of about one atmosphere is commonly maintained across the membrane. Typically, the feed or charge side of the membrane is at about atmospheric pressure and the permeate or discharge side of the membrane is at a pressure of about 1-20 preferably 1-10, say 2 mm.Hg.

The permeate which passes through the membrane includes water and a small proportion of the other components of the charge liquid. Typically, the permeate contains 90-99.9, say 99 w % water. Permeate is recovered in vapor phase.

Pervaporation may typically be carried out at a flux of 0.1-1, say 0.20 gallons per square foot per day which corresponds to about 0.17-1.7, say 0.34 kilograms per square meter per hour (kmh). Typically, the units may have selectivity (measured in terms of w % water in the permeate) of 96-99.9%, say 99.8%.

The separation Factor S or Sep which represents the ability of the membrane to separate water is calculated as follows:

$$S = \frac{\left(\frac{X_n}{X_m}\right)_p}{\left(\frac{X_n}{X_m}\right)_f}$$

wherein $X_n$ and $X_m$ are the weight fractions of water and non-aqueous components respectively in the permeate (P) and the feed (F). A system showing no separation at all would have a Separation Factor of 1; and a system showing perfect 100% separation would have a Separation Factor of infinity. The process of the instant invention may commonly have a Separation Factor of about 1000-70,000, typically 7000-61,000, say about 42,000. Satisfactory operation appears to require a Separation Factor of at least about 1000 although good commercial practice would require Separation Factors about 7000 or above. The process of this invention typically yields Separation Factors which are greater than this.

Practice of the process of this invention will be apparent to those skilled in the art from inspection of the following examples wherein, as elsewhere in this specification, all parts are parts by weight unless otherwise stated.

DESCRIPTION OF SPECIFIC EMBODIMENTS

EXAMPLES I-III

In this series of examples, Example I of which represents the best mode presently known of carrying out the process of this invention, the selective separating layer was mounted on the porous support layer of a commercially available (from Daicel Chemical Industries) composite bearing, as a porous support layer, microporous polyacrylonitrile ultrafiltration membrane of molecular weight cut-off of 20,000. The selective separating layer was formed in situ by a one-step coating process. The separating layer was formed from an aqueous solution containing 10 g of 7 w % polyvinyl alcohol (m.w. of 115,000) and 10 g of 7 w % polyacrylic acid (m.w. of 250,000). This 50 w/50 w mixture was stirred until homogeneous and spread onto the polyacrylonitrile microporous support to form a film 4 mils thick. The assembly was cured in an oven for 10 minutes at 150° C.

The membrane was evaluated in pervaporation cells to which the charge at 60° C. was a mixture of methyl ethyl ketone and toluene (2:1 weight ratio) containing 2.3% water. Permeate pressure was 2 mm.Hg.

In Examples II and III, the procedure of Example I was followed except that the weight ratio of polyvinyl alcohol to polyacrylic acid in the non-porous separating layer was different: Example I was 1:1 (i.e. 50/50); Example II was 0.43: 1 (i.e. 30/70); and Example III was 2.33:1 (i.e. 70/30)

The concentration of water in the permeate was measured; the Separation Factor (Sep) and the Flux (kmh) in kilograms per square meter per hour at 60° C. are reported:

TABLE

| Example | Ratio | % water in permeate | Sep | Flux kmh |
| --- | --- | --- | --- | --- |
| I | 1 | 99.9 | 42,440 | 0.36 |
| II | 0.43 | 99.8 | 21,200 | 0.36 |
| III | 2.33 | 98.8 | 3,500 | 0.3 |

From the above table, it is apparent that as the weight ratio of polyvinyl alcohol to polyacrylic acid is varied, the water content of the permeate, the Separation Factor, and the Flux vary. It is noted that the system of Example I, characterized by the 50:50 weight ratio of polyvinyl alcohol to polyacrylic acid shows results which are superior to those of Examples II-III.

EXAMPLES IV-V-VI

In this series of Examples, the procedure of Examples I-III was followed except the (i) the separating layer did not contain polyacrylic acid and (ii) the polyvinyl alcohol employed had a molecular weight $\overline{M}_n$ of 96,000. For cross-linking, a 25 w % aqueous solution of glutaraldehyde (at a mole ratio of glutaraldehyde to polyvinyl alcohol of 0.2) was added in the presence of 0.5N of sulfuric acid at a mole ratio of acid to glutaraldehyde of 0.1.)

The membranes were cured at various temperatures and times and subjected to pervaporation at 70° C. with the same charge as was charged to Examples I–III.

TABLE

| Example | Curing Temp %C | Time Min | Feed w % water | Permeate % water | Sep | Flux kmh |
|---|---|---|---|---|---|---|
| IV | 150 | 10 | 2 | 99.3 | 6950 | 0.24 |
| V | 125 | 15 | 2 | 98.6 | 3450 | 0.25 |
| VI | 105 | 15 | 2 | 98.7 | 3720 | 0.21 |

From the above table, it is apparent that although satisfactory results are achieved in each of Examples IV–VI, best results are attained in Example IV in which the polyvinyl alcohol separating membrane is cured at 150° C. for 10 minutes. The water content of the permeate and the Separation Factor are significantly higher; and the flux is satisfactory.

It will also be noted that the PVA/PAA, membranes of Examples I–III give better results than are attained by the PVA membranes of Examples IV–VI.

EXAMPLES VII*-VIII*-IX*

In this series of control Examples, the membrane system is similar to that of Examples I–VI except that in Examples VII*-IX*, the membrane is formed from the Nafion-H 117 brand of perfluorinated resin membrane made by Dupont characterized by a thickness of 190 microns and having the structure

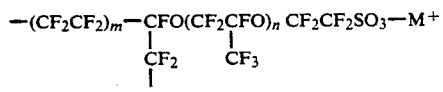

In each control Example, the membrane was treated with treating agent by exposing the membrane to a solution for 24 hours at 20° C. followed by three thirty minute washes to remove any treating agent and equilibration in charge solutions. In control Example VII*, the treating agent was a 0.2 M aqueous solution of cesium bromide CsBr followed by washing in water. In control Example VIII*, the treating agent was 0.2 M aqueous solution of lithium bromide LiBr followed by washing in water. In control Example IX*, the treating agent was a 0.2 M solution of tetrabutyl ammonium bromide $(Bu)_4NBr$ in water followed by washing in water.

These ion-exchange systems were subjected to pervaporation at 50° C. to determine their ability to separate small concentrations of water from a 1:1 mixture of MEK-Toluene:

TABLE

| Example | Membrane | Feed % water | Permeate % water | Sep | Flux kmh |
|---|---|---|---|---|---|
| VII* | Nafion-Cs | 1.2 | 87.6 | 580 | 0.05 |
| VIII* | Nafion-Li | 1.1 | 73.6 | 250 | 0.07 |
| IX* | Nafion-NBu$_4$ | 1.3 | 83.1 | 370 | 0.06 |

From the above table, it is apparent that the membranes of Control Examples VII*-IX* are much less satisfactory than are the membranes of this invention with respect to Separation Factor and Flux.

EXAMPLES X*-XI*-XII*

In this series of Control Examples, the membrane system is similar to that of Examples I–III except that in Examples X*, XI*, and XII*, the membrane is a commercially available polyvinyl alcohol membrane marketed by Gemeinschaft Fur Trenntechnik. This membrane is a non-porous membrane as set forth in Eur. Patent 96 330 to GFT as assignee of Bruschke.

These membrane systems were subjected to pervaporation at 70° C. to determine their ability to separate small concentrations of water from a 1:1 mixture of MEK-toluene.

TABLE

| Example | Membrane | Feed % water | Permeate % water | Sep | Flux kmh |
|---|---|---|---|---|---|
| X* | GFT-1 | 1.0 | 95.8 | 2260 | 0.01 |
| XI* | GFT-2 | 1.1 | 95.5 | 1910 | 0.01 |
| XII* | GFT-3 | 1.1 | 96.2 | 2280 | 0.02 |

A comparison of the above Table with the Tables Supra showing the results of Examples I–III and IV–VI of the systems of the instant invention reveals that the membranes of the instant invention are superior to the membranes of Examples X*-XII* with respect to Separation and Flux.

EXAMPLES XIII-XVI

In this series of experimental examples, the PVA membrane system of Example IV is used in pervaporation at 80° C. of a 2:1 MEK-toluene system; and the content of water (w %) in the feed is varied to determine the effect on Separation and Flux.

TABLE

| Example | Feed % water | Permeate % water | Sep | Flux kmh |
|---|---|---|---|---|
| XIII | 2.5 | 96.0 | 940 | 0.29 |
| XIV | 2.0 | 96.7 | 1440 | 0.27 |
| XV | 1.8 | 97.1 | 1830 | 0.27 |
| XVI | 1.4 | 96.0 | 1690 | 0.22 |

From the above Table, it is apparent that, as the concentration of water in the Feed decreases, (at a pervaporation temperature of 80° C.) the concentration of water in the permeate (i.e. the Selectivity) changes very little and the Flux decreases. The Separation Factor generally is greater at lower water content reaching a peak of 1830.

EXAMPLES XVII-XX

In this system of experimental examples, the PVA/PAA membrane system of Example I is used in pervaporation at 60° C. of a 2:1 MEK-toluene system; and the content of water (w %) in the feed is varied to determine the effect on Separation and Flux.

TABLE

| Example | Feed w % water | Permeate % water | Sep | Flux kmh |
|---|---|---|---|---|
| XVII | 2.3 | 99.9 | 42440 | 0.36 |
| XVIII | 2.0 | 99.9 | 48950 | 0.24 |
| XIX | 1.8 | 99.9 | 54500 | 0.09 |
| XX | 1.6 | 99.9 | 61440 | 0.08 |

From the above table, its apparent that, as the concentration of water in the Feed decreases (at a pervaporation temperature of 60° C.), the concentration of water in the permeate (i.e. the Selectivity) remains unchanged, the Separation Factor desirably increases substantially, and the Flux undesirably decreases.

EXAMPLES XXI-XXV

In this series of experimental Examples, the membrane system of Example IV is used in pervaporation of a 2:1 MEK-toluene charge. Separation Factor, Flux, and water content of the permeate are measured as a function of the temperature of pervaporation.

TABLE

| Example | Temp °C. | Feed w % water | Permeate w % water | Sep | Flux kmh |
|---|---|---|---|---|---|
| XXI | 80 | 2 | 96.7 | 1440 | 0.27 |
| XXII | 70 | 2 | 99.3 | 6950 | 0.24 |
| XXIII | 60 | 2 | 98.3 | 2830 | 0.18 |
| XXIV | 50 | 2 | 98.3 | 2830 | 0.15 |

From the above Table, it is apparent that as the temperature of pervaporation decreases, Flux decreases. Both Selectivity (as measured by the water content of the Permeate) and the Separation Factor reach a peak at 70° C.

Results comparable to those attained with Example I-VI may be attained when the charge liquid is as follows:

TABLE

| Example | Charge Liquid |
|---|---|
| XXV | 70% methyl ketone |
|  | 15% toluene |
|  | 15% benzene |
|  | containing 3 w % water |
| XXVI | 60% ethanol |
|  | 40% gasoline |
|  | containing 2 w % water |
| XXVII | 20% methanol |
|  | 20% ethanol |
|  | 60% gasoline |
|  | containing 1 w % water |
| XXVIII | 20% methyl t-butyl ether |
|  | 80% gasoline |
|  | containing 1 w % water |

Results comparable to those attained with Examples IV-VI may be attained when the cross-linking agent (in place of glutaraldehyde) is as follows:

TABLE

| Example | Cross-linking Agent |
|---|---|
| XXIX | 2-hydroxy hexanedial-1,6 |
| XXX | malonic dialdehyde |
| XXXI | succinic dialdehyde |
| XXXII | hexanedial-1,6 |

Although this invention has been illustrated by reference to specific embodiments, it will be apparent to those skilled in the art that various charges and modifications may be made which clearly fall within the scope of the invention.

We claim:

1. The method of separating water from a charge aqueous mixture of hydrocarbon and organic oxygenate which comprises maintaining a non-porous membrane separating layer of (i) a blend of polyvinyl alcohol and a polyacrylic acid or consisting of (ii) cast polyvinyl alcohol which has been cross-linked with an aliphatic polyaldehyde containing at least three carbon atoms including those in said aldehyde groups;

maintaining a pressure drop across said non-porous separating layer;

passing a charge water-containing solution of hydrocarbon and organic oxygenate into contact with the high pressure side of said non-porous separating layer whereby at least a portion of said water in said charge aqueous mixture and a lesser portion of hydrocarbon and organic oxygenate pass by pervaporation through said non-porous separating layer as a lean mixture containing more water and less hydrocarbon and organic oxygenate than are present in said charge aqueous mixture and said charge aqueous mixture is converted to a rich liquid containing less water and more hydrocarbon and organic oxygenate than are present in said charge aqueous mixture;

recovering from the low pressure side of said non-porous separating layer said lean mixture containing more water and less hydrocarbon and organic oxygenate than are present in said charge aqueous mixture, said lean mixture being recovered in vapor phase at a pressure below the vapor pressure thereof; and recovering from the high pressure side of said non-porous separating layer said rich liquid containing a lower water content and a higher hydrocarbon and organic oxygenate content than are present in said charge aqueous mixture.

2. The method claimed in claim 1 wherein said aliphatic polyaldehyde is a $C_3$–$C_6$ aliphatic dialdehyde.

3. The method claimed in claim 1 wherein said aliphatic polyaldehyde is glutaraldehyde.

4. The method claimed in claim 1 wherein said non-porous separating layer is a blend of polyvinyl alcohol and a polyacrylic acid.

5. The method claimed in claim 1 wherein said hydrocarbon is toluene.

6. The method claimed in claim 1 wherein said hydrocarbon is a gasoline.

7. The method claimed in claim 1 wherein said organic oxygenate is methyl ethyl ketone.

8. The method claimed in claim 1 wherein said organic oxygenate is ethanol or methanol.

9. The method of separating water from a charge aqueous mixture containing toluene and methyl ethyl ketone which comprises maintaining a non-porous membrane separating layer of a blend of polyvinyl alcohol and a polyacrylic acid;

maintaining a pressure drop across said non-porous separating layer;

passing a charge aqueous mixture of toluene and methyl ethyl ketone into contact with the high pressure side of said non-porous separating layer whereby at least a portion of the water is said charge aqueous mixture and a lesser portion of toluene and methyl ethyl ketone pass by pervaporation through said non-porous membrane separating layer as a lean mixture containing more water and less toluene and methyl ethyl ketone than are present in said charge aqueous mixture and said charge aqueous mixture is converted to a rich liquid containing less water and more toluene and methyl ethyl ketone than are present in said charge aqueous mixture;

recovering from the low pressure side of said non-porous separating layer said lean mixture containing more water and less toluene and methyl ethyl ketone than are present in said charge aqueous mixture, said lean mixture being recovered in vapor phase at a pressure below the vapor pressure thereof; and recovering from the high pressure side of said non-porous separating layer said rich liquid containing a lower water content and a higher toluene and methyl ethyl ketone content than are present in said charge aqueous mixture.

* * * * *